United States Patent
Zimdars et al.

(10) Patent No.: US 7,449,695 B2
(45) Date of Patent: Nov. 11, 2008

(54) TERAHERTZ IMAGING SYSTEM FOR EXAMINING ARTICLES

(75) Inventors: David A. Zimdars, Ann Arbor, MI (US); Greg Stuk, Saline, MI (US); Steven L. Williamson, Ann Arbor, MI (US)

(73) Assignee: Picometrix, Ann Arbor, MI (US)

(*) Notice: Subject to any disclaimer, the term of this patent is extended or adjusted under 35 U.S.C. 154(b) by 131 days.

(21) Appl. No.: 11/138,246

(22) Filed: May 26, 2005

(65) Prior Publication Data

US 2007/0235658 A1 Oct. 11, 2007

Related U.S. Application Data

(60) Provisional application No. 60/574,643, filed on May 26, 2004.

(51) Int. Cl.
*G01J 5/02* (2006.01)
*G01F 23/00* (2006.01)

(52) U.S. Cl. ............... 250/341.8; 250/341.7; 250/359.1

(58) Field of Classification Search ............ 250/390.07, 250/359.1, 341.7, 341.8
See application file for complete search history.

(56) References Cited

U.S. PATENT DOCUMENTS

| | | | |
|---|---|---|---|
| 4,199,222 A | | 4/1980 | Ikushima et al. |
| 4,639,075 A | | 1/1987 | Salour et al. |
| 4,845,730 A | * | 7/1989 | Mercer ........................ 378/53 |
| 4,937,449 A | * | 6/1990 | Kreuzer et al. ............... 250/351 |
| 5,077,477 A | * | 12/1991 | Stroman et al. ............. 250/349 |
| 5,127,072 A | | 6/1992 | Blauvelt et al. |
| 5,389,789 A | * | 2/1995 | Nguyen .................... 250/341.1 |
| 5,401,953 A | | 3/1995 | Spencer et al. |
| 5,420,595 A | | 5/1995 | Zhang et al. |
| 5,539,322 A | | 7/1996 | Zoughi et al. |
| 5,623,145 A | | 4/1997 | Nuss |
| 5,663,639 A | | 9/1997 | Brown et al. |
| 5,689,361 A | | 11/1997 | Damen |
| 5,698,978 A | | 12/1997 | Darling et al. |
| 5,710,430 A | | 1/1998 | Nuss |
| 5,715,263 A | | 2/1998 | Ventrudo et al. |
| 5,729,017 A | | 3/1998 | Brener et al. |

(Continued)

FOREIGN PATENT DOCUMENTS

DE 44 15 269 A1 11/1995

(Continued)

OTHER PUBLICATIONS

Z. Jiang, X.C. Zhang, THz Imaging via Electro-Optic Effect, IEEE MTT-S Digest, 1999, pp. 941-944.

(Continued)

*Primary Examiner*—David P. Porta
*Assistant Examiner*—Carolyn Igyarto
(74) *Attorney, Agent, or Firm*—Brinks Hofer Gilson & Lione

(57) ABSTRACT

A system to detect an article includes one or more terahertz modules. Each module either generates or receives, or both generates and receives, terahertz radiation. Some of the terahertz radiation is reflected from the article and the remainder of the terahertz radiation is transmitted through the article. A processor analyzes the reflected and transmitted terahertz radiation to characterize the article.

26 Claims, 8 Drawing Sheets

U.S. PATENT DOCUMENTS

| | | | |
|---|---|---|---|
| 5,789,750 A | 8/1998 | Nuss | |
| 5,859,535 A | 1/1999 | Liu | |
| 5,872,447 A | 2/1999 | Hager, III | |
| 5,886,534 A | 3/1999 | Bakhtiari et al. | |
| 5,894,124 A | 4/1999 | Iwabuchi et al. | |
| 5,894,125 A | 4/1999 | Brener et al. | |
| 5,920,588 A | 7/1999 | Watanabe | |
| 5,923,174 A | 7/1999 | Darling, Jr. | |
| 5,929,644 A | 7/1999 | Sokolov | |
| 5,933,014 A | 8/1999 | Hartrumpf et al. | |
| 5,939,721 A | 8/1999 | Jacobsen et al. | |
| 6,005,397 A | 12/1999 | Zoughi et al. | |
| 6,008,658 A | 12/1999 | Suyama et al. | |
| 6,013,915 A * | 1/2000 | Watkins | 250/341.1 |
| 6,078,047 A | 6/2000 | Mittleman et al. | |
| 6,109,108 A | 8/2000 | Ohtani et al. | |
| 6,320,191 B1 | 11/2001 | Rudd | |
| 6,388,799 B1 | 5/2002 | Arnone et al. | |
| 6,507,309 B2 * | 1/2003 | McMakin et al. | 342/22 |
| 6,717,717 B2 | 4/2004 | Nelson | |
| 6,815,683 B2 * | 11/2004 | Federici et al. | 250/341.1 |
| 6,816,647 B1 | 11/2004 | Rudd et al. | |
| 6,828,558 B1 * | 12/2004 | Arnone et al. | 250/341.1 |
| 6,849,852 B2 | 2/2005 | Williamson | |
| 7,087,902 B2 * | 8/2006 | Wang et al. | 250/341.1 |
| 7,145,506 B2 * | 12/2006 | Holt et al. | 342/179 |
| 7,235,766 B2 * | 6/2007 | Shur et al. | 250/205 |
| 2001/0038074 A1 | 11/2001 | Zhang et al. | |
| 2002/0162962 A1 * | 11/2002 | Rudolph | 250/339.1 |
| 2003/0011871 A1 | 1/2003 | Nelson | |
| 2003/0149346 A1 | 8/2003 | Arnone et al. | |
| 2003/0155512 A1 | 8/2003 | Arnone et al. | |
| 2003/0165003 A1 | 9/2003 | Ciesla et al. | |
| 2003/0178584 A1 | 9/2003 | Arnone et al. | |
| 2004/0065832 A1 | 4/2004 | Cluff et al. | |
| 2004/0065833 A1 * | 4/2004 | Torgrip et al. | 250/341.7 |
| 2004/0095147 A1 | 5/2004 | Cole | |
| 2004/0155665 A1 | 8/2004 | Arnone et al. | |
| 2005/0082479 A1 | 4/2005 | Wallace et al. | |
| 2005/0100866 A1 | 5/2005 | Arnone et al. | |
| 2005/0156110 A1 | 7/2005 | Crawely | |
| 2005/0156120 A1 | 7/2005 | Arnone et al. | |

FOREIGN PATENT DOCUMENTS

| | | |
|---|---|---|
| EP | 0 841 548 A2 | 5/1998 |
| EP | 0 828 143 A2 | 11/1998 |
| EP | 1 190 234 A1 | 3/2002 |
| EP | 1 224 506 A1 | 7/2002 |
| EP | 1 259 795 A1 | 11/2002 |
| EP | 1 269 156 A1 | 1/2003 |
| EP | 1 297 321 A1 | 4/2003 |
| EP | 1 352 287 A2 | 10/2003 |
| EP | 1 356 263 A2 | 10/2003 |
| EP | 1 428 011 A2 | 6/2004 |
| EP | 1 474 675 A2 | 11/2004 |
| EP | 1 536 531 A1 | 11/2004 |
| EP | 1 537 604 A1 | 6/2005 |
| EP | 1 537 606 A1 | 6/2005 |
| EP | 1 537 636 A1 | 6/2005 |
| EP | 1 543 372 A1 | 6/2005 |
| GB | 2 360 842 A | 10/2001 |
| GB | 2 360 842 B | 6/2002 |
| GB | 2 371 618 A | 7/2002 |
| GB | 2 372 929 A | 9/2002 |
| GB | 2 372 930 A | 9/2002 |
| GB | 2 372 929 B | 3/2003 |
| GB | 2 372 930 B | 3/2003 |
| GB | 2 380 920 A | 4/2003 |
| GB | 2 384 555 A | 7/2003 |
| GB | 2 385 415 A | 8/2003 |
| GB | 2 392 779 A | 3/2004 |
| GB | 2 393 037 A | 3/2004 |
| GB | 2 393 260 A | 3/2004 |
| GB | 2 396 695 A | 6/2004 |
| GB | 2 397 207 A | 7/2004 |
| GB | 2 399 626 A | 9/2004 |
| GB | 2 393 260 B | 12/2004 |
| GB | 2 402 471 A | 12/2004 |
| GB | 2 405 200 A | 2/2005 |
| GB | 2 405 263 A | 2/2005 |
| GB | 2 405 466 A | 3/2005 |
| GB | 2 397 207 B | 4/2005 |
| GB | 2 384 555 B | 5/2005 |
| GB | 2 392 779 B | 5/2005 |
| GB | 2 396 695 B | 5/2005 |
| GB | 2 409 026 A | 6/2005 |
| GB | 2 409 104 A | 6/2005 |
| GB | 2 410 613 A | 8/2005 |
| GB | 2 411 093 A | 8/2005 |
| JP | 50-124878 | 10/1975 |
| JP | 3-71306 | 7/1991 |
| WO | WO/99/49297 | 9/1999 |
| WO | WO/01/06915 | 2/2001 |
| WO | WO/01/38929 | 5/2001 |
| WO | WO/01/48457 | 7/2001 |
| WO | WO 02/061398 A2 | 8/2002 |
| WO | WO 2004/034533 A1 | 4/2004 |
| WO | WO/2004/083796 | 9/2004 |

OTHER PUBLICATIONS

S. Hunsche, D.M. Mittleman, M. Koch, M.C. Nuss, New Dimensions in T-Ray Imaging, IEICE Trans. Electron., V. E81-C, No. 2, Feb. 1998, pp. 269-275.

N. Froberg et al., Terahertz Radiation from a Photoconducting Antenna Array, vol. 28, No. 10, Oct. 1992 IEEE Journal of Quantum Electronics.

R. Lai et al., A photoconductive, miniature terahertz source, vol. 72, No. 24, Jun. 15, 1998, American Institute of Physics.

Y. Pastol et al., Characterisation of an Optoelectronically Pulsed Equiangular Spiral Antenna, vol. 26, No. 2, Jan. 1990, Electronics Letters.

M. Feuer et al., 100 GHz Wafer Probes Based on Photoconductive Sampling, vol. 5, No. 3, Mar. 1993, IEEE Photonics Technology Letters.

M.H. Moore, R.L. Hudson, Far-Infrared Spectral Studies of Phase Changes in Water Ice Induced by Proton Irradiation, The Astrophysical Journal, 401, Dec. 10, 1992, pp. 353-360.

Globus Tatiana, et al., "Optical Characteristics of Biological Molecules in the Terahertz Gap," Database Compendex Online!, Engineering Information, Inc., New York, NY, US; XP002341336, Database accession No. E2005169050736, abstract.

Globus Tatiana, et al., "Optical Characteristics of Biological Molecules in the Terahertz Gap," Proceedings of SPIE, Chemical and Biological Standoff Detection II, vol. 5584, Oct. 27, 2004, pp. 1-10.

Min Ki Choi, et al., "Potential for Detection of Explosive and Biological Hazards with Electronic Terahertz Systems," Philosophical Transactions of the Royal Society of London, Series A (Mathematical, Physical and Engineering Sciences) R. Soc. UK, vol. 362, No. 1815, Feb. 15, 2004, pp. 337-359.

Zimdars, D., et al., "Terahertz Reflection Imaging for Package and Personnel Inspection," Database Inspec Online!, The Institution of Electrical Engineers, Stevenage, GB; 2004, XP002341337, Database accession No. 8395880, abstract.

Zimdars, D., et al., "Terahertz Reflection Imaging for Package and Personnel Inspection", Proceedings of the SPIE—The International Society for Optical Engineering SPIE-Int. Soc. Opt. Eng USA, vol. 5411, No. 1, Apr. 12-13, 2004, pp. 78-83.

Zimdars D.A.. "Fiber-pigtailed Terahertz Time Domain Spectroscopy Instrumentation For Package Inspection and Security Imaging," Proceedings of the SPIE—The International Society For Optical Engineering, vol. 5070, 2003, pp. 108-116.

Hartwick T.S., et al. "Far Infrared Imagery", Applied Optics USA, vol. 15, No. 8, Aug. 1976, pp. 1919-1922.

Kemp, M.C. et al., "Security Applications of Terahertz Technology", Proceedings f the SPIE—The International Society For Optical Engineering, vol. 5070, 2003, pp. 44-52.

Mittleman D.M., et al. "T-Ray Imaging", IEEE Journal of Selected Topics in Quantum Electronics, vol. 2, No. 3, Sep. 1996, pp. 679-692.

* cited by examiner

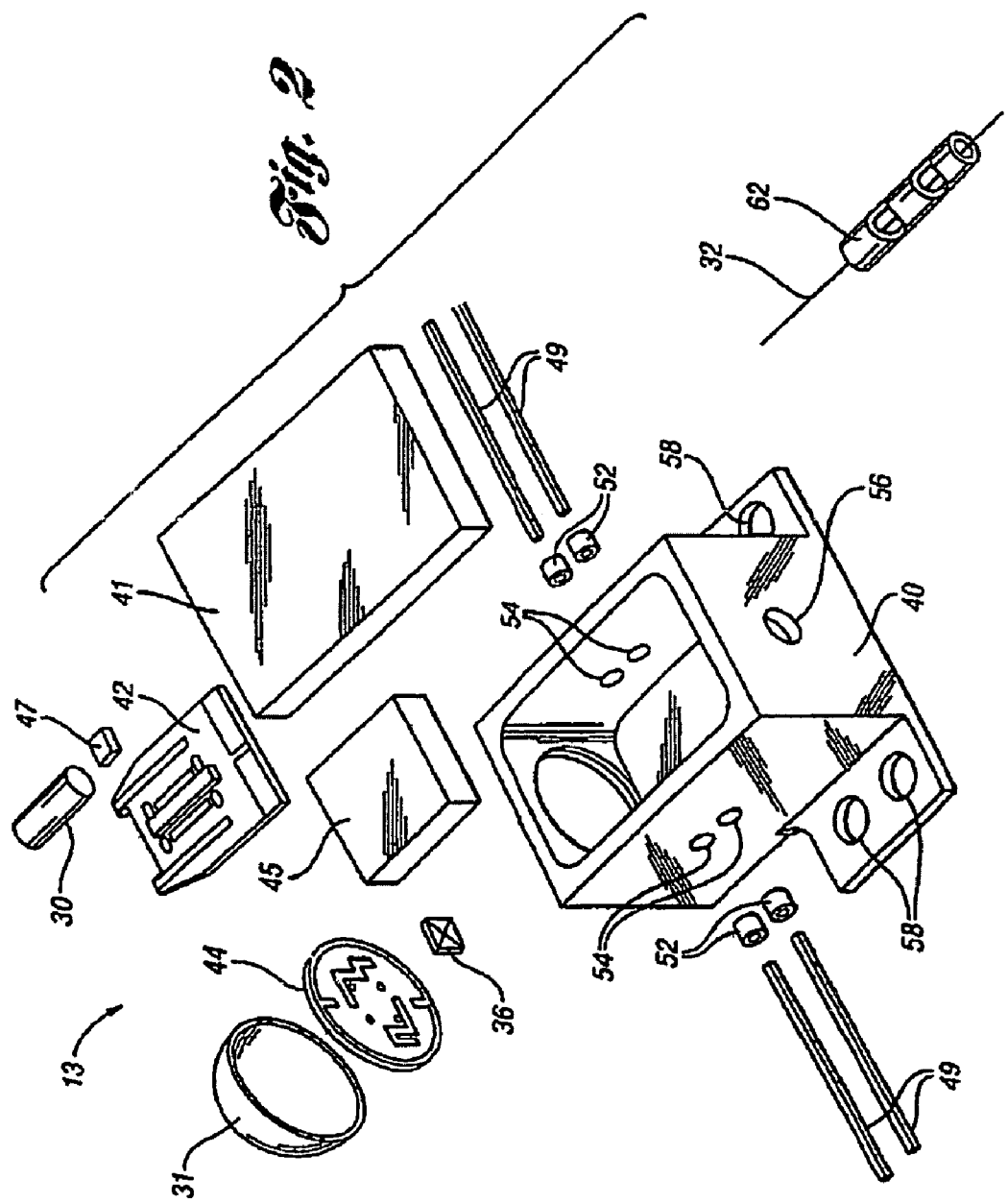

TERAHERTZ IMAGING SYSTEM FOR EXAMINING ARTICLES

RELATED APPLICATION

This application claims the benefit of U.S. Provisional Application No. 60/574,643, filed May 26, 2004, the entire contents of which are incorporated herein by reference.

BACKGROUND

This invention relates to systems using terahertz radiation to detect particular types of articles.

Computerized tomography (CT) imaging has been employed for non-destructive examination of various types of articles, such as contraband, which may be hidden inside luggage. However, CT systems emit X-rays, which may pose a health risk to the operators of such systems, as well as passengers who may be standing near the system, and hence CT systems generally include some type of shield to protect the operators and passengers ionizing radiation. Moreover, although CT systems are capable of analyzing the density of an article, along with other characteristics of the shape and volume of the article, these systems do not have spectroscopic capabilities, and therefore cannot analyze the chemical compositions of the articles. Furthermore, X-rays are not sensitive to the optical traits that result from the article's refractive index and absorption coefficient. These properties, if measurable, can yield unique, high-contrast images and reveal much about the reflective, absorptive and scattering properties of material.

Thus, there is a need for a non-destructive imaging system that is also capable of providing optical and spectroscopic probing capabilities.

BRIEF SUMMARY OF THE INVENTION

In general, the present invention is directed to a system and methods of its operation for detecting articles, which may be hidden or embedded within other objects, materials or substances. The system includes one or more terahertz modules. Each module either generates or receives, or both generates and receives, terahertz radiation. Some of the terahertz radiation is reflected from the article and the remainder of the terahertz radiation is transmitted through the article. A processor analyzes the reflected and transmitted terahertz radiation to characterize the article. The processor can form a two-dimensional or three-dimensional image, or both two and three dimensional images of the article. The processor can form a pixel or a voxel, or both a pixel and a voxel, of a specific region of the article.

In certain embodiments, the system employs terahertz time domain spectroscopy in either reflection or transmission modes, or in both modes, in which an article is probed by terahertz radiation. The article may be probed at only one location or many locations to form a two or three dimensional image of the article. The article may be naked explosive material or explosives concealed within wrappers, packages, luggage, clothing or other items. Thus, terahertz radiation is used for detecting objects, materials and/or substances either exposed or concealed within other objects, materials or substances. The articles are identified by one or more of several analyses of the transmitted or reflected radiation. The analyses of the radiation may include the pulse time-of-flight, attenuation, reflection, refraction, diffraction, scattering, change in polarization or spectral content.

Embodiments of the system may include one or more of the following advantages. The system is capable of analyzing material texture, its frequency-dependent refractive index (dielectric constant), frequency-dependent absorption, birefringence, shape, and volume of an article. In addition, the system may provide other spectral information of the article. The THz machine employs no ionizing radiation, and therefore requires no shielding. Where X-ray radiation (or other penetrating forms of probing radiation) are available, fusion of their images with the THz images will further increase the system's overall accuracy in detecting articles.

BRIEF DESCRIPTION OF THE DRAWINGS

FIG. 1b is a top view of a portion of the system of FIG. 1a.

FIG. 2 is an exploded isometric view of an embodiment of a terahertz module, in accordance with the present invention.

FIG. 4b is a top-conceptual terahertz image of a layer profile slice generated from the reflected pulse train of FIG. 6a.

FIG. 5b depicts the amplitude spectrum of the THz waveform shown in FIG. 5a.

DETAILED DESCRIPTION

Figure 1A:
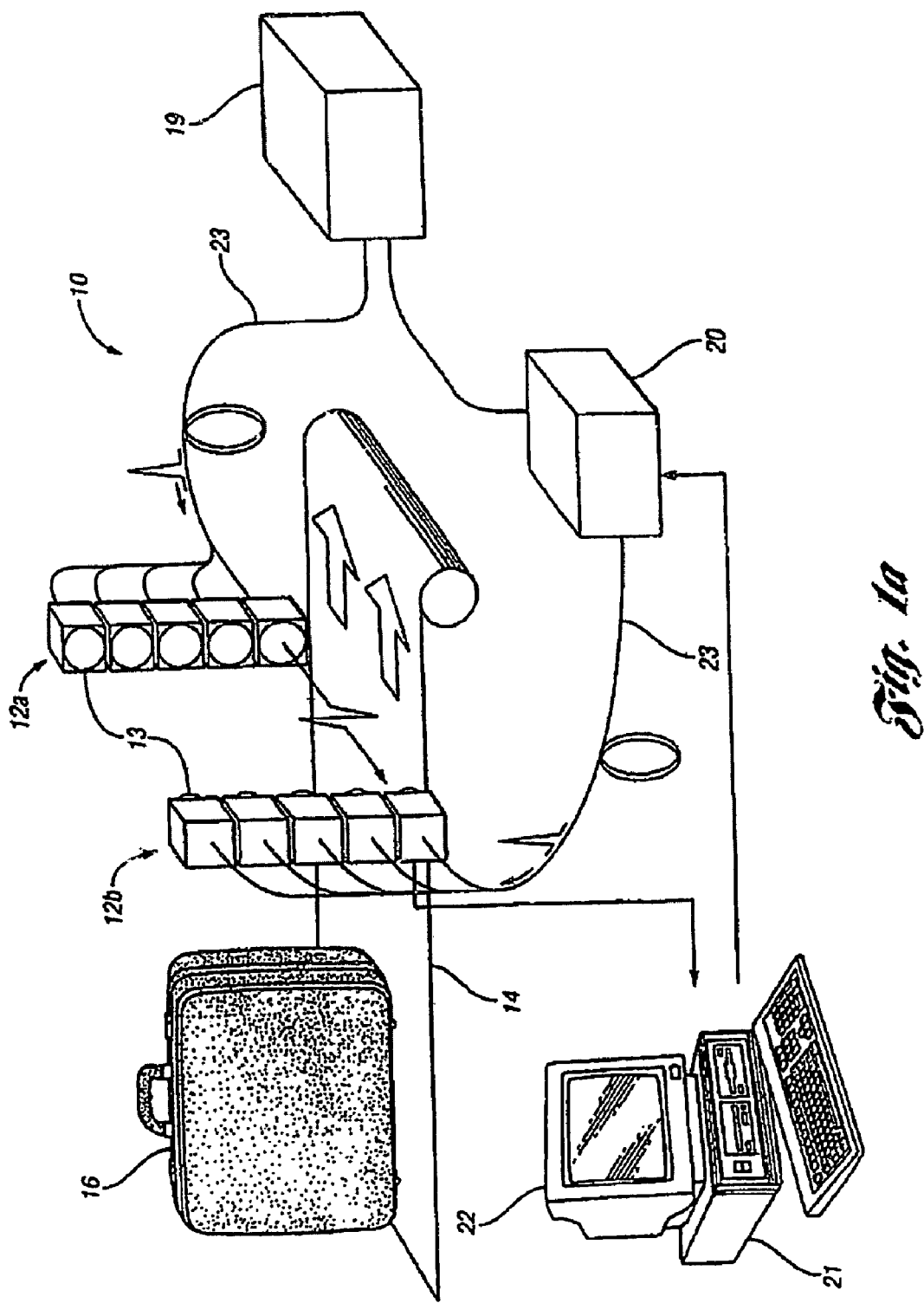
FIG. 1a is a diagrammatic view of a terahertz electromagnetic radiation emission and detection system in accordance with the invention.
Figure 1B:
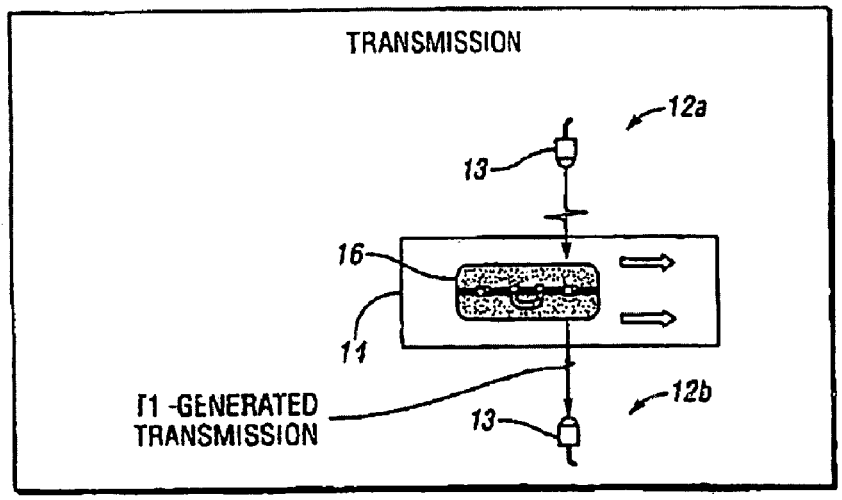

Referring now to the drawings, a system embodying the principles of the present invention is illustrated in FIGS. 1a and 1b, and is generally designated at 10. The system 10 is a terahertz (THz) imaging and spectroscopy explosive detection system using time domain analysis for luggage scanning. The system 10 includes one or more arrays of terahertz modules, such as arrays 12a and 12b, that emit and/or receive terahertz radiation (T-rays) to image contents of luggage and detect the explosive signature of an article possibly located inside the luggage. A belt 14 moves the bags 16 through the arrays 12a and 12b. Because of the high speed belt, the system 10 can be enclosed for safety purposes. However, no radiation shielding is required and an open system can be implemented for easy operator access to the bags. The system 10 also includes a fiber-coupled laser 19, such as a femtosecond laser, an optical delay 20 that allows the THz pulses generated by 12a to be accurately synchronized to the moment that the THz receiver, 12b is excited, or switched on, a processor 21, such as a computer for data acquisition and analysis, and a human-machine interface 22. The interface is where the operator is shown the images of package contents and is informed of the presence of explosives, flammable liquids, chemical weapons, contraband and other hazards.

In a particular implementation, each of the arrays 12a and 12b includes 2 groups of 3 staggered 128 terahertz transmitter/receiver modules 13 arranged linearly and operating, preferably, in the range between about 0.01-10 THz. Thus, the system 10 uses 3 linear arrays 12a consisting of 128 emitting modules 13 and another 3 linear arrays 12b consisting of 128 receiving modules 13 to receive the THz signals to interrogate luggage passing through the system 10. Each module 13 in the respective arrays independently generates or receives a THz beam of approximately 2.25 mm diameter yielding a line scan width of about 3×128×2.25 mm, or 860 mm. A second system of linear arrays can be configured in the same manner as 10, though orthogonally disposed from 10 to provide simultaneous THz probing of bags along the orthogonal axis as the belt moves the bag past both sets of sensors. This configuration would thus allow the bags to be scanned both horizontally and vertically. Reflection waveforms are obtained for about 300 mm of depth on each side (for a total of about 600 mm), requiring the acquisition of an approximately 2000 ps waveform at about 150 Hz. Belt speed is then about 0.3 m/s, providing a scan rate of approximately 1450 bags/hour with a pixel resolution of about 2.25 mm square.

In some implementations, the source 19 and optical delay 20 are coupled by fiber optic cables 23 to the modules 13. The source 19 can be a Ti:sapphire pulsed laser. Alternatively, any pulsed laser which is capable of producing an optical pulse of less than about 2 picoseconds and preferably less than about 0.2 picosecond in duration may be substituted for the pulsed Ti:sapphire laser as the source 19. For example, the lasers described in U.S. Pat. No. 5,880,877, the entire contents of which are incorporated herein by reference, may be used as the source 19. Thus, lasers such as a Ti:Sapphire laser, a Cr:LiSAF laser, a Cr:LiSGAF laser, a Cr:LiSCAF laser, an Er-doped Fiber laser, an Yb-doped fiber laser and gain switched diode laser are appropriate for use as the source 19. Moreover, the system 10 is usable with a continuous wave optical source (in place of the femtosecond laser) as described in U.S. Pat. No. 5,663,639, the entire contents Of which are incorporated herein by reference. The terahertz modules 13 can be of any kind described in U.S. Pat. No. 5,789,750, the entire contents of which are incorporated herein by reference.

Figure 3:
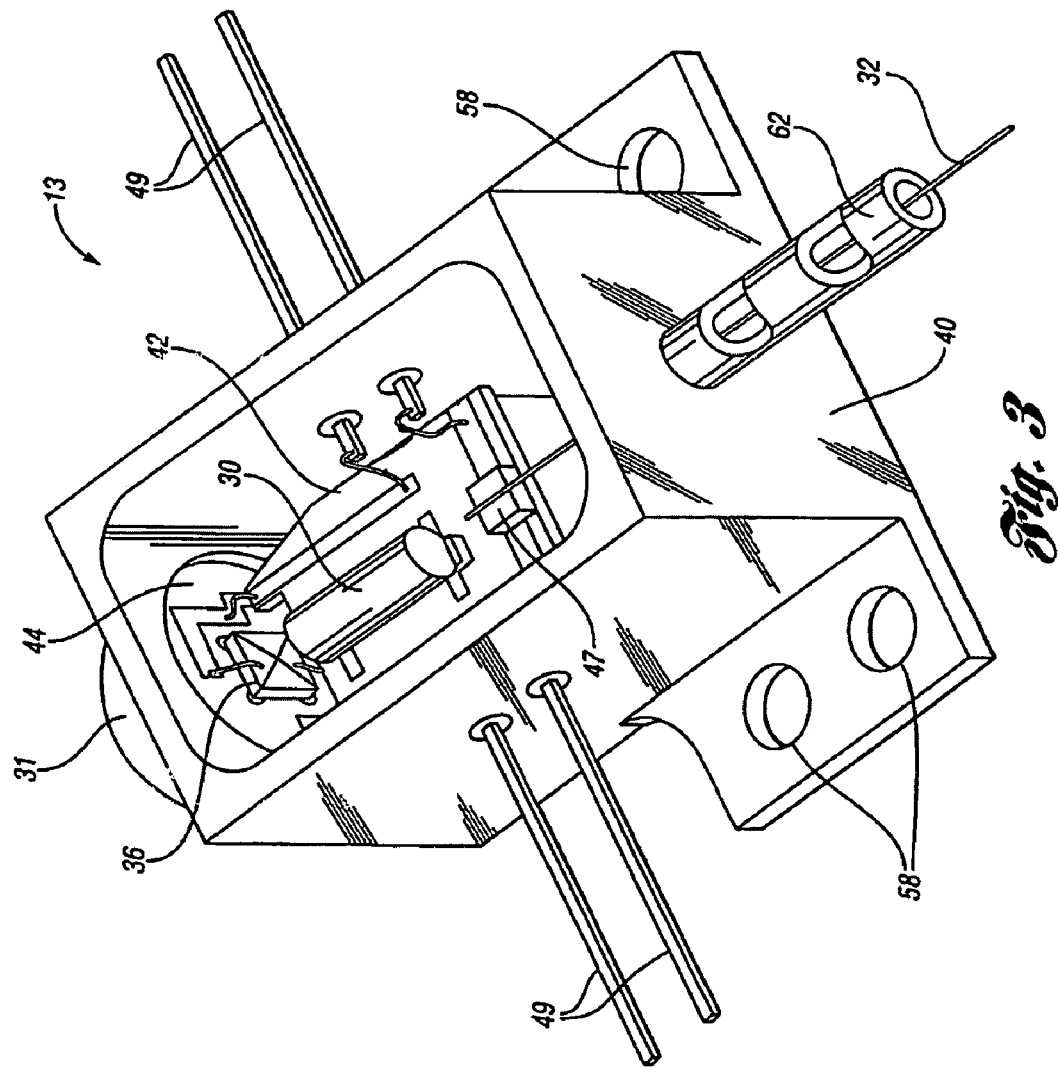
FIG. 3 is an assembled isometric view of an embodiment of the terahertz module, in accordance with the present invention.

FIGS. 2 through 3 illustrate an embodiment of the terahertz modules 13. As shown, a terahertz device 36 is mounted within each terahertz module 13 for generating and/or detecting the electromagnetic radiation. The terahertz device 36 has a pair of electrodes and bonded to a low-temperature-grown Gallium Arsenide semiconductor substrate or other suitable substrate material. The module 13 further includes a relay optic 30, such as a GRIN lens, which serves the dual purpose of making the device easier to manufacture and also helps focus the output of an optical fiber 32 down to the optimal spot size. Furthermore, the relay optic 30 (or other intermediate optic) removes the fiber 32 from the immediate vicinity of the terahertz device 36, which in the case of the transmitter, could cause the emitted terahertz radiation to couple into the fiber 32 rather than into the transmitter substrate.

An industrial hardened case or housing 40 having a lid 41 seals the system to protect it from environmental variables and rough handling. A plurality of electrical conductor pins 49 are bonded to electrically insulating bushings 52 which are pressed into and bonded to bushing apertures 54 in housing 40. A fiber aperture 56 is disposed in the case 40 and is configured to receive a ferrule 62 having fiber 32 bonded thereto. A plurality of mounting apertures 58 are also provided in the case 40 to mechanically secure terahertz module 13 to a mounting surface.

The terahertz module 13 also includes an optic mounting plate or launcher 42 that may be made from alumina or other suitable material. Plate 42 holds the optical relay 30, a fiber pillow block 47 and fiber 32 in place as well as providing electrical contacts for the device. A carrier or window 44 is also provided for ease of assembly of the terahertz device to the module. Window 44 can be easily fabricated using standard micro-fabrication techniques and can be made from silicon or an other compatible material. The window 44 can be soldered or bonded to the case 40. A silicon, sapphire, alumina, or other style of terahertz lens 31 is mounted onto the back of window 44 for reducing the divergence of the electromagnetic wave radiation emanating from the terahertz device 36. The lens 31 configuration is generally aplanatic, although an aspherically-shaped coupling lens can be used to improve collimation or focus the THz beam.

A riser block 45 and the fiber pillow block 47 are provided to position the mounting plate 42 and the fiber 32, respectively, to the appropriate height above a bottom inside surface of the case 40 to insure optical fiber alignment with the relay optic 30 and the terahertz device 36. The riser block 45 can be integrated into the bottom floor of the module thus, reducing component piece count.

Further details of terahertz transceivers are provided in U.S. Pat. No. 6,816,647, issued Nov. 19, 2004, the entire contents of which are incorporated herein by reference.

In a particular embodiment, each terahertz module 13 is a miniature fiber-optic pigtailed hermetically sealed T-Ray antenna module manufactured to Telcordia telecommunications standards. On the front of each module, there is a silicon aplanatic hyperhemispherical lens to efficiently couple the THz pulse into free space. This lens can also be aspherical to provide diffraction-limited focusing capability. Behind the lens is a LT-GaAs photoconductive THz antenna. Other semiconductors, including ion-implanted silicon-on-sapphire, Er:GaAs, LT-InGaAs or Be:GaAs could also be used. The optical pulse is focused onto the photoconductor by a permanently aligned fiber. A custom computer controlled fiber-optic soldering station with sub-micron resolution may be employed to manufacture these modules. These T-Ray modules can be configured in a multitude of T-Ray array configurations, such as those shown in FIG. 1.

Figure 1C:
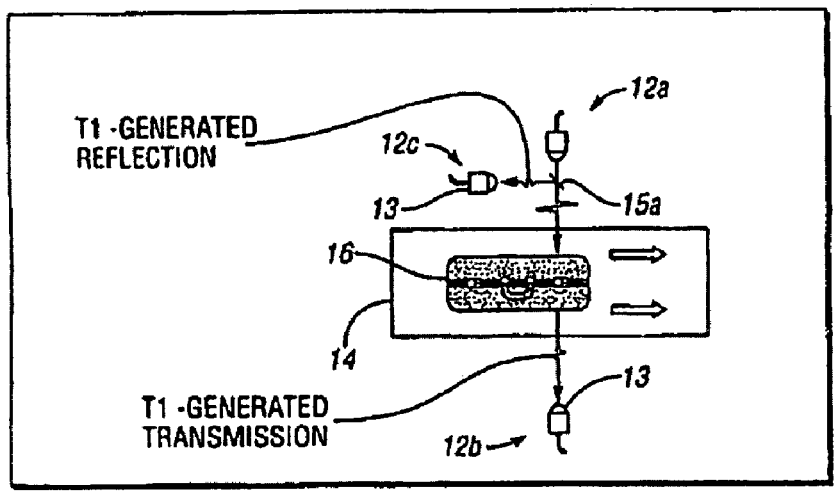
FIG. 1c is a top view of an alternative arrangement of terahertz modules in accordance with the invention.

In a particular implementation, as shown in FIG. 1c, the system 10 interrogates the sample or article by generating T-rays from the modules 13 in the array 12a to form THz images in two modalities: a transmission mode and a reflection mode. In the transmission mode, THz pulses travel completely through the luggage and are received by the modules 13 in the array 12b. The spectrally-dependent amplitude and time delay of the transmitted pulse are analyzed to represent a single pixel, which when added to the other pixels yields a two dimensional image of the luggage being scanned. In the reflection mode, the THz pulses reflect off the interfaces of the material layers comprising the bag's content, and a series of return pulses from these layers are reflected by a partially-reflective beam-spitting mirror 15a towards module 13 configured in an array 12c and detected in sequence by the modules 13 in the array 12c. This sequence of pulses is utilized to construct a three dimensional image of the object. The depth resolution is less than about 1 mm, but can be scaled to about 2.25 mm, yielding about a 2.25 mm cubed volume pixel (i.e., a "voxel"). The characteristic signatures of an explosive in its spectral absorption, time delay (index of refraction), specific extinction coefficient and reflectivity can be used separately of in combination to identify an explosive within a particular pixel or a voxel.

Figure 1D:
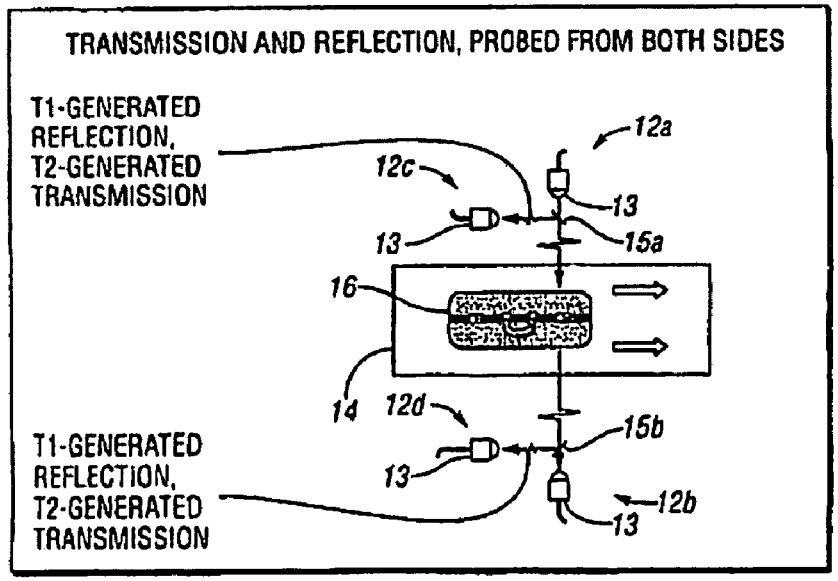
FIG. 1d is a top view of another alternative arrangement of terahertz modules in accordance with the invention.

In another implementation, as shown in FIG. 1d, the modules in both the arrays 12a and 12b generate terahertz radiation. Modules 13 in an array 12d receive transmitted terahertz radiation from the array 12a that is directed to the array 12d by a mirror 15b and reflected terahertz radiation (originally generated by the array 12b) that is also directed to the array 12d by the mirror 15b. In addition, the modules 13 in an array 12c receive transmitted terahertz radiation from the array 12b that is directed to the array 12c by a mirror 15a and reflected terahertz radiation (originally generated by the array 12a) that is also directed to the array 12c by the mirror 15a. The transmitted and reflected radiation is then analyzed as described above.

Accordingly, the system 10 is an explosive device detection configuration employing terahertz time domain spectroscopy in either reflection, transmission or both where material is probed by the THz pulses with spectral content in the range or a subset of the range between about 0.05 THz and 10 THz. Material may be probed at only one location or many locations to form a two or three dimensional image. The material may be naked explosive material or explosives concealed within wrappers, packages, luggage, clothing or other items. Thus, terahertz radiation is used for detecting articles such as objects, materials and/or substances either exposed or concealed within other objects, materials or substances. Explosives are identified using one or more of several methods of analysis of the transmitted or reflected pulse, where the pulse time-of-flight, reflectivity, change in polarization, attenuation, and spectral content are some of the properties of the material probed: 1) the transmitted pulse is analyzed for the known THz spectral signatures of the explosives; 2) the reflected pulse is analyzed for the known THz spectral signatures of the explosives; 3) the transmission image is analyzed for structure corresponding to an explosive; 4) the reflection image is analyzed for structure corresponding to an explosive; 5) the index of refraction within a volume is analyzed to be the same as an explosive; 6) the attenuation within a volume is analyzed to be the same as an explosive. The material may be probed with THz pulses configured for transmission or reflection tomography in order to compute the material properties 1) through 6) from above for a small volume. Broadband THz pulses are utilized because concealing material may attenuate some of the higher frequency spectral content of the pulse. However, some portion of the pulse will transmit allowing the properties 1) through 6) to be analyzed.

Terahertz waves, which lie between the microwave and infrared region of the spectrum, can penetrate clothing, leather, plastic, ceramics, paper, cardboard, and other common materials. The system 10 uses terahertz imaging to reveal concealed explosives; metallic and non-metallic weapons (such as ceramic, plastic or composite guns and knives); flammables; biological agents; chemical weapons and other threats hidden in luggage. In addition to having superior chemical specificity in comparison to X-Ray imaging, terahertz imaging employs safe non-ionizing radiation which reduces the need for safety shielding. Images can have sub-millimeter resolution, similar to the human eye at a short distance. Explosives, chemical weapons, and biological agents possess spectral signatures in the terahertz regime, and the broadband terahertz images obtain the entire spectra for each voxel. This allows an operator to identify a bomb, for example, not only by inspecting several uniquely-contrasting images of the explosive device beneath the clothing, but also by spectroscopic indication of explosive material comprising the bomb. Preferably, explosives can appear as a special "color" to the operator. That is, the "color" indicates an alarm to the operator that explosive material may have been detected.

Figure 4A:
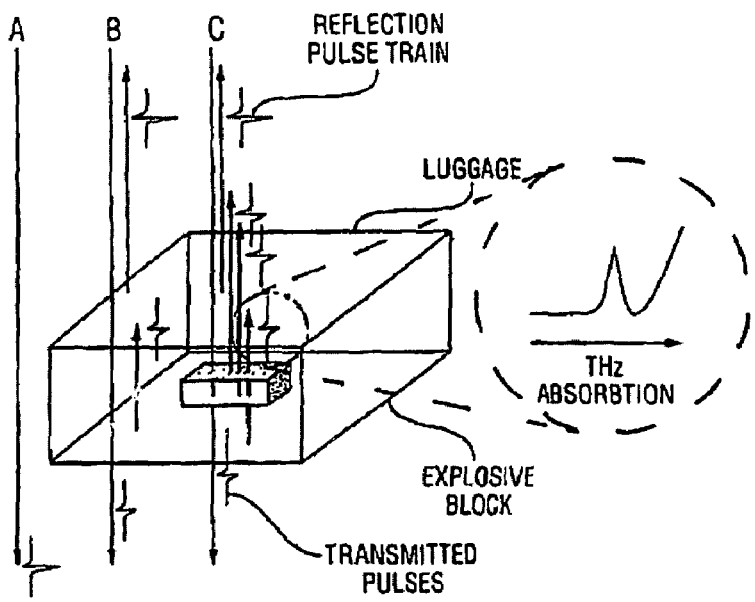
FIG. 4a is an illustration of THz transmission and reflection imaging of explosives in luggage showing three THz beam paths: (A) outside the luggage, (B) through luggage and ordinary contents, and (C) through luggage and explosive block, transmitted THz pulses being shown exiting through the luggage on the bottom, and the reflected THz pulse trains being shown exiting from the top.

In accordance with the invention, THz transmission and reflection imaging of luggage for explosives detection with the system 10 is illustrated in FIG. 4a. In this example, a luggage bag approximately 600 mm×800 mm×300 mm, with a buried 25 mm×50 mm×75 mm brick of explosive exhibits a THz signature (for example, the brick can be RDX exhibiting a feature at 0.8 THz in reflection spectrum, and an indicative attenuation and index of refraction transmission). Three different THz pulse paths, "A", "B", and "C", are shown. The other paths from a linear array or scanning system are not explicitly shown for clarity. The pulse path "A" does not pass through the luggage. The pulse path "B" travels through the luggage, but not through the explosive block. The pulse pass "C" travels through the luggage and the explosive block.

Figure 4B:
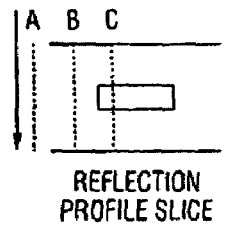
Figure 4C:
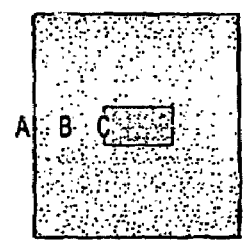
FIG. 4c is a bottom-conceptual two dimensional transmission terahertz image calculated from time of flight and attenuation.

The transmitted pulses are shown in paths "A", "B", and "C" as exiting through the bottom of the luggage. In this example, no path is sufficiently attenuated or blocked by a mirror (metal) that would otherwise shield the transmitted pulses. Three analytical methods can be applied to the transmitted pulses: 1) pulse propagation time which is proportional to the amount of mass (refractive index) in the path; 2) attenuation/reflection of the pulses is related to the mass, scattering, and chemical composition; 3) frequency domain spectra is related to the chemical composition. The two-dimensional transmission image in FIG. 4c is hypothetically constructed from the analysis of each path in the grid matrix through the luggage.

The reflected pulses are shown in paths "A", "B", and "C" as exiting through the top of the luggage. A portion of the generated THz pulse will reflect from each interface between two materials. Interfaces between differing materials such as air-clothing or clothing-explosive block will produce strong reflections. Reflections from similar interfaces such as clothing-clothing will be present but weaker. Each of the three transmission analyses: propagation, attenuation, and spectra can be applied to each of the reflected pulses from each layer in sequence. The thickness of each layer can be calculated from the pulse propagation time, and utilizing the polarity of the reflected pulse, an algorithm can be developed to determine the density of each layer. Each of the return pulses is successively attenuated. Additionally, reflected pulses can carry spectral signatures, which can be used to identify explosives and trigger an alarm. The reflection profile slice shown in FIG. 4b illustrates a single cross section containing paths "A," "B," and "C", constructed from the reflection pulse trains. The reflected spectra, see inset, has a signature of an explosive, and combined with consistent density and attenuation information, has triggered an alarm (hence, the explosive is colored, for example, in red). The full 3D reconstruction can be realized by combining the series of lateral slices.

Conventional computerized tomography (CT) X-Ray imaging can detect explosives by analyzing the density of a volume element, along with other characteristics of shape and volume. The system 10 is also capable of utilizing the same density analyses, and provide an alarm when explosives are detected. In addition, the system 10 provides retrievable high quality spectral information of shallow explosives. This feature provides additional discriminatory information to increase the likelihood of providing an alarm on a true positive and not on a false negative. Unlike spinning CT X-Ray sensors, the THz linear array can be static (and it is possible to construct a true two-dimensional array as well), which results in a greater theoretical imaging speed. The system 10 employs no ionizing radiation, requiring no shielding. Thus, the system 10 may provide for faster inspection with lower false alarms and at a reduced cost and size.

In accordance with the invention, the system 10 shown in FIGS. 1a and 1b is only one of several configurations employing THz transmission and reflection spectroscopy and imaging to detect explosives. In accordance with the invention, other configurations employ THz electro-optic generation and/or detection instead of or at the same time as photoconductive generation and/or detection. The modules 13 may operate as transmitters or receivers, or as both (i.e., as transceivers), and can employ resonant or non resonant antennas, such as dipoles, bow-ties, log-spirals or others.

The system 10 can also be driven using one or more fixed-frequency or tunable CW lasers in place of the pulsed laser. In this case, tunable CW THz radiation would be generated and coherently received by the modules 13 instead of the pulsed THz radiation. The system 10 can also utilize all-electronic or semiconductor-based THz generation systems such as non-linear transmission lines, quantum cascade laser structures, electronic oscillators and gas lasers, to name a few. Also, non-coherent and coherent THz detection techniques can be used, including bolometers, thermal couples, diode structures, and small-bandgap detectors, to name a few. The system can employ one or more THz transmitters and one or more THz receivers. The transmitter(s) can be configured in point, linear, 2-D, axial, or other array configurations. The receiver(s) can be configured in point, linear, 2-D, axial, or other array configurations. One or more banks of transmitters and receiver arrays can be configured for transmission and/or reflection. The transmitters and receivers may be free space, fiber optic or waveguide coupled in the THz spectral region. The transmitters and receivers may be driven optically by free space, fiber optic, or waveguide coupled femtosecond laser source or continuous wave radiation source. The object being scanned can be stationary or moving. The transmitters and receivers may be stationary (for example direct 2-D array image generation), moving or raster scanned. The transmitters and receivers can be configured into a wand or other hand-held, freely-positionable device for portability and agility of use when scanning large objects or non-stationary objects such as people.

The THz optical system may include reflective or refractive elements or a combination of both. The image can be generated by direct pixel assignment of a scalar computed value at each sampled location, or through a computed tomography algorithm to compute a scalar value for each volume element (voxel). After an image has been constructed, a more extensive measurement at a particular location can be made. This could take the form of dwelling for a longer period of time at a particular voxel to obtain an enhance spectrum. The scanning optical delay (time over which the received pulse is sampled) can be a fixed window encompassing all or part of the delay between pulses, or the optical delay window can track (a depth profile, for example). For a femtosecond laser driven system, one or more laser sources may be employed in either the transmitter and/or receiver drives. One or more optical amplifier systems can be employed. The optical laser system can be fiber optic coupled, free space, or integrated in whole or in part into the transmitter or receiver package. The system 10 may be combined with other probing diagnostic techniques such as X-ray, mass spectrometer, and metal detection.

The use of THz radiation for sensing and for image formation in the system 10 may offer a variety of advantages over other more conventional imaging methods. For example, terahertz radiation represents the highest frequencies for which the propagating electric field E(t) (rather than merely the field's intensity $|E(t)|^2$) can be measured directly. As a result, using THz rays for imaging permits phase-sensitive measurement at the highest possible spatial resolution. Also, many materials exhibit unique spectral signatures in the THz range, so spectroscopic imaging, sensing, and identification are all feasible. Terahertz radiation is non-ionizing and biologically benign, so its implementation in a crowded environment poses fewer health and safety concerns than, for example, X-Ray imaging. THz imaging is non-contact, and can easily work through cloth, vacuum, foams, insulation, and other materials with poor propagation of sound, which might hamper ultrasound techniques.

Figure 5A:
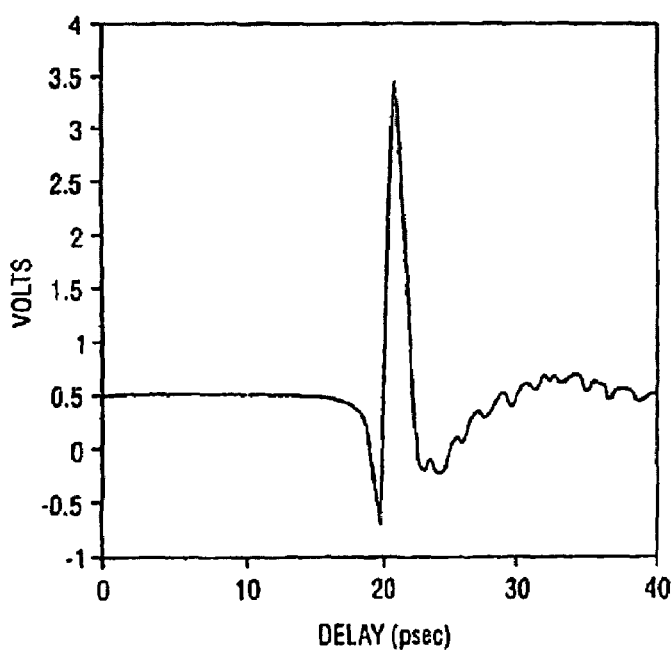
FIG. 5a depicts a THz waveform measured in the time domain (psec).
Figure 5B:
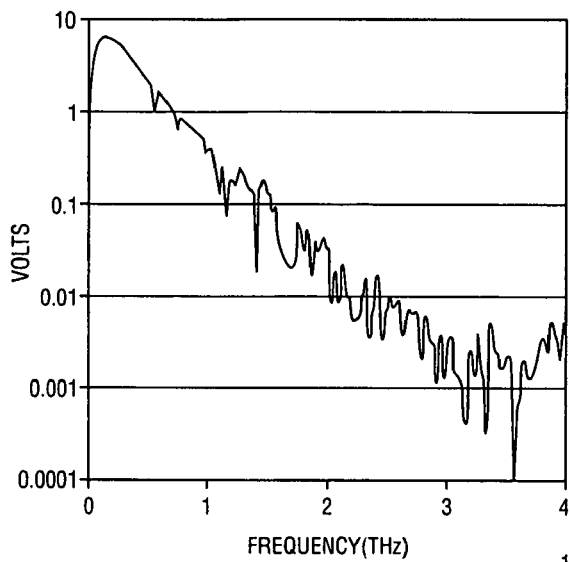
Figure 6A:
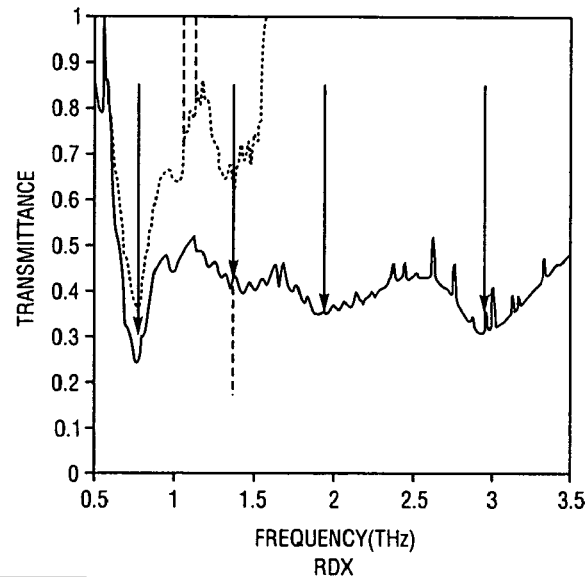
FIGS. 6a-6e depict transmission spectra of explosives RDX (transmittance and extinction), HMX (extinction), PETN (extinction), and TNT (extinction) in the range between about 0.1 and 3 THz.
Figure 6B:
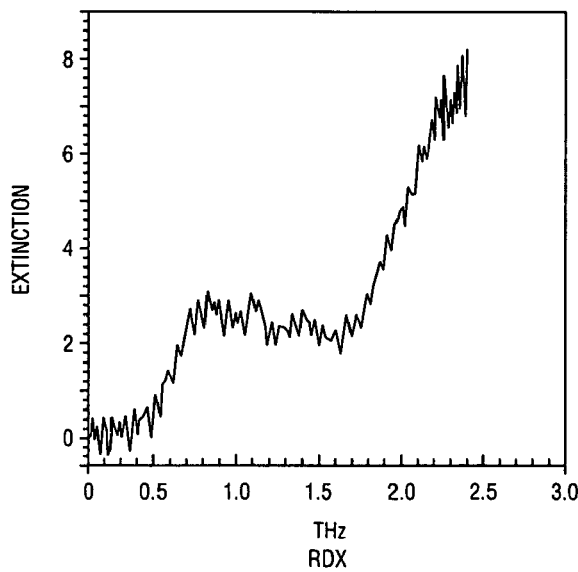
Figure 6C:
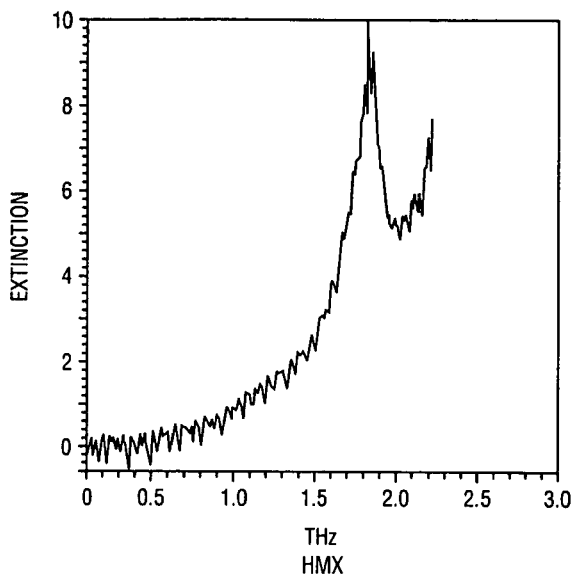
Figure 6D:
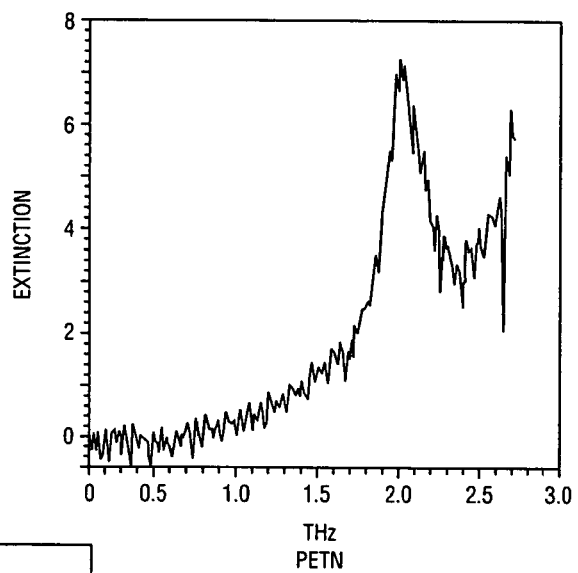
Figure 6E:
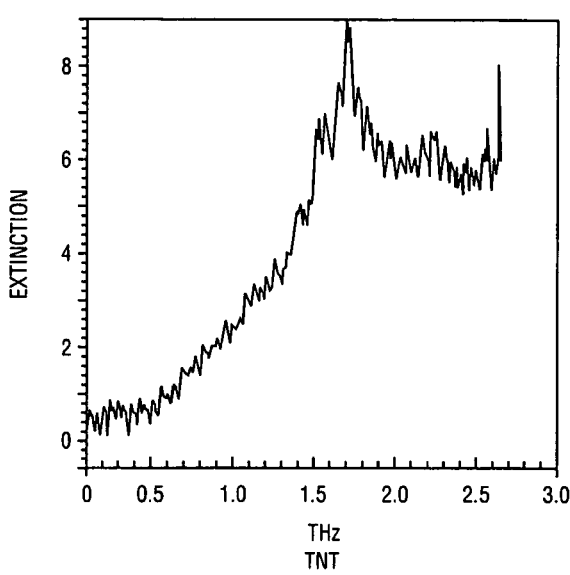

The system 10 employs terahertz time-domain spectroscopy and imaging (THz-TDS), for example, the use of an ultrafast laser and optoelectronics to provide generation and detection of broadband single-cycle pulses in the terahertz frequency range. A femtosecond optical pulse can be used to gate a terahertz antenna consisting of a pair of coplanar strip lines photolithographically defined on a semiconducting substrate, with an integrated dipole antenna. The gate pulse induces a transient current across the gap, which radiates in the THz spectral range, as shown in FIG. 5a (THz waveform in the time domain) and FIG. 5b (corresponding amplitude and phase of the waveform's Fourier transform). The emitted THz beam exhibits high spatial coherence, and may be collected, collimated, and focused using conventional optics. It easily propagates through dry air of several meters without significant distortions. These pulses are detected using a coherent gated sampling method. Synchronization of the femtosecond pulses used to excite the transmitter and receiver is accomplished using an optical delay 20 (FIG. 1). The receiver antenna, similar to the transmitter, is optically gated with a synchronized femtosecond pulse from the optical source. This effectively shorts the antenna gap, so that the incoming THz pulse can induce a photocurrent. This photocurrent, measured as a function of the delay between the THz pulse and gating optical pulse, is proportional to the THz electric field E(t).

Although explosives may be detected in THz images of luggage through relative transmission and time-of-flight measurements of density, the utilization of THz spectroscopy identifies explosives reliably with fewer false positives and negatives because explosives have been shown to have spectral signatures in the THz region.

As shown in FIGS. 6a-6e, several explosives have characteristic transmission spectral signatures consisting of one or more broad absorption lines between 0.1 and 3 THz. As shown, the spectra of secondary explosive 1,3,5 trinitro-s-triazine (RDX) using both time domain THz spectroscopy and Fourier transform infrared spectroscopy (FTIR) depict a broad absorption feature at 0.8 THz. Additionally, the spectra of HMX, PETN, and TNT are shown, all with characteristic THz absorption features. The thickness of the explosive material measured in transmission was typically 250 microns and correspondingly the extinction coefficients, of these explosives are quite large above 0.5 THz. In order to access all of the transmission absorption lines up to 3 THz, the explosives are only a few millimeters thick, providing the best signal-to-noise ratio. The absorption below 0.5 THz is several orders of magnitude lower, allowing many centimeters of penetration in this region. Given the strong extinction in transmission, the explosive spectra may be best identified in reflection. The explosives exhibit corresponding spectral features in reflection (corresponding to the change in index with frequency as well as absorption). Utilizing the time-of-flight properties of the time domain THz signal enables identifying the explosives utilizing signatures in addition to (or instead of) the frequency domain absorption spectral lines. The explosives are typically much denser than layers of clothing, and correspondingly delay the time of flight of the THz pulse through the explosive layers much more than clothing alone. Preliminary data indicate that at low frequencies the explosives are less absorptive than clothing, but more absorptive than a corresponding thickness of plastic. Thus, FIGS. 6a-6e indicate that THz signatures may be used either alone, or as part of a sensor incorporated with CT X-Ray, can identify explosives and reduce false alarm rates.

Some materials common to luggage (such as metal) block or shield THz beams. In this case, the transmission image is not available, but the single-sided reflection image is still usable. Other materials, with increasing thickness, partially absorb or scatter the THz radiation, which limits penetration depth. Other than true shields, penetration is a matter of signal-to-noise ratio, which is a trade-off of transmission power, receiver noise, and dwell time (baggage processing rate). In general, unless a true shield blocks layers beneath it, both THz transmission and reflection images, utilizing time-of-flight analysis and reflection amplitude is possible (in the time domain). Systems which identify threats and explosives by image (shape) or index of refraction (time-of-flight) is effective at all penetration depths. In general, some of the THz signal's frequency spectrum will penetrate, even if most of the spectrum is blocked.

Note that the ability to identify explosives by their frequency domain spectra, by either transmission or reflection, depends on whether or not the spectra are blocked, obscured, or confused by intervening material. Metal, conductive material (solid without gaps), and water (>250 microns thick) completely block the THz beam from penetrating, and the interior of any volume completely enclosed by these materials cannot be imaged. Although the transmission image is blocked, these materials (including water) are quite reflective, and the reflection image up to the blocking layer is still available.

The system 10 concerns the detection of explosives using time domain terahertz (TD-THz) spectroscopy and/or imaging. The system 10 and its operation can be referred to as a time domain terahertz explosive detection system (TD-THz EDS). The system 10 enables the automated detection of explosives concealed within or on luggage, handbags, parcels, packages, letters, containers, crates, clothing, shoes, personnel and all other modes where for security purposes or where otherwise it is desirable to sense explosives and emit an alarm when explosives are detected. While the system 10 enables automated detection of explosives, the system 10 and its operation can be in whole or in part implemented in either automated or non-automated fashion. Moreover, while many elements of the system 10 concern the detection of concealed explosives, the system 10 improves the detection of non-concealed explosives.

The system 10 examines items either in a throughput (or point) detection mode or in stand-off detection mode. In a throughput system, the items or people to be tested are brought to the system either manually or automatically, and are conveyed to and/or past the sensing system (for example, luggage going into a machine on a belt or people walking through a portal). In a stand-off implementation, the EDS sensors examine a target (such as a person) at some distance.

The system 10 collects data from its sensors and automatically judges the probable absence or probable presence of explosives. Operator participation in this judgment process is not required, or may be as minimal as possible. Automated detection improves throughput, reduces error, and reduces the number of operators.

An item under test by the system 10 consists of material that is entirely explosives, partly explosives and partly benign, or entirely benign. In the case of detecting concealed explosives (in luggage, for example) in most security operations nearly all items under test are entirely benign. Those rare items, which have concealed explosives, still consist mostly of benign material.

In general, the criteria for detection (i.e., the emission of an alarm) uses some threshold. As discussed below, it is often desirable not to emit an alarm on the minimum possible detectable quantity of explosives, but rather define a minimum quantity, spatial configuration, or some other combination of physically measurable parameters which correspond to sufficiently indicate that there is enough explosives to do significant damage or to probably consist of a bomb (rather than trace residue or non-threatening object). By extending the criteria beyond the mere molecular presence of explosives, the automatic detection by the system 10 may be improved. These criteria define set of concealed material and objects within an item under test which set off an alarm (and by definition exclude all other benign material and objects). The physical criteria which cause an alarm is called the explosive alarm configuration.

If in an automated mode, a true positive occurs when the system 10 examines an item meeting the explosive alarm configuration and properly emits an alarm. If the system 10 fails to set off an alarm, a false negative has occurred.

If the system 10 examines an item which does not meet the explosive alarm configuration and does not set off an alarm, a true negative has occurred. And a false positive occurs when the system 10 improperly emits an alarm.

Thus, when considering the results of many examined items, the system 10 has a probability of a true positive and a probability of a false positive (where the probability of a false negative is 1-false positive, and likewise the probability of a true negative is 1-false positive).

Hence, it is desirable to have the probability of a true positive to be as high as possible (near unity), such that no threats are missed. Likewise it is desirable to have the probability of false positives to be very low, such that many hand searches are not required among other reasons.

In accordance with the invention, an automated alarm is made based on meeting a statistical threshold and decision algorithm based on the analysis of one or more parameters the sensor data of the system 10. If the probability of a true positive is too low, the statistical threshold and decision algorithm can be adjusted (i.e., made less stringent) to more readily generate an alarm. This, however, has the undesirable effect of increasing the probability of a false positive. (Taken to the extreme, the system 10 could be set to always alarm, with the effect that the probability of a true positive is 1, but the probability of a false positive is also 1.) Therefore, it is desirable to have a set of sensor data with sufficient contrast between explosives and benign material and sufficiently correlateable with other defining parameters to allow the highest threshold of excluding the possible presence of the explosive alarm configuration.

The TD-THz pulse from the system 10, whether in transmission or reflection, illuminates all or a portion of the sample. Automated detection can be enhanced when in the transmission or reflection mode, the TD-THz transmitters and receivers are configured in a manner to collect a 1-, 2-, or 3-dimensional image or "map" of the sample. The raw data collected for this map consists of the THz waveforms recorded in transmission or reflection corresponding to multiple locations on the sample. The sensor system can be configured with a single transmitter-receiver pair which is raster scanned in one or two dimensions from one or multiple views. Or, the sensor system may include a linear array or axial array which may be scanned, or a 2D array which can be scanned.

The THz waveforms provided from the sensors probing one or more locations are processed by algorithm(s) to compute one or more pixel values for each location corresponding to generic physical measurements or empirical quantities for each location within the spatial 1-, 2-, or 3-dimensional data map. In reflection, TD-THz reflection tomographic methods are used to compute the 1-, 2- or 3-dimensional spatial information. In transmission, computed axial or computed linear tomography are used to compute the 1-, 2- or 3-dimensional spatial information. This can be applied to any technique, such as synthetic aperture techniques.

The values in the data map may include one or more of 1-, 2- or 3-dimensional pixel values such as (i) attenuation and/or reflectivity at one or more frequencies, (ii) index of refraction of one or more frequencies, and (iii) time-of-flight, dielectric constant, scattering coefficients, spectroscopic data and density (grams per cubic centimeter); and the algorithms produce results in a 1-, 2- or 3-dimensional matrix, with the output from each data reduction algorithm being generic and containing user-specified control properties such as pixel dimension (volume or area), averaging, precision, region of time domain THz waveform processed, number of frequency bands and frequency resolution.

A feature of TD-THz imaging of the system 10 is that one or more of these calculated physical measurements can be classified where a range of values may belong to an explosive while another range of values belongs to benign material. These ranges may be used to identify specific explosives, or may serve to classify the set of explosive materials belonging to the previously mentioned explosive alarm configuration. They may be calculated from reference spectra or measurements, or may be adjusted entirely empirically to yield an explosive detection algorithm, which has an acceptable true positive and false positive alarm probability.

This data map is then processed by an explosive detection algorithm, which may utilize threshold values for these ranges for each of the measurements at each location in the data map. The explosive detection may emit an alarm on each of the individual elements in the data map individually, or it may consider them in groups or in aggregate to provide an acceptable true positive and false positive alarm probability. That is, the spatial information provided can be correlated with the individual pixel values statistically to enhance the explosive alarm criteria. As an example, set requirements may include:

1) the of number individual pixels meeting explosive threshold individually within a volume or area is greater in number or an average value than some aggregate threshold value; and/or
2) the volume or area of individual pixels meeting explosive threshold individually within a volume or area is sufficiently contiguous and does not include voids of benign material; and/or
3) the 1-, 2- or 3-dimensional geometry of a grouping of individually alarming pixels meats some threshold criteria; and/or
4) other criteria correlating the spatial relationship of the individual elements of the data map to their spatial distribution within the data map.

The TD-THz EDS system 10 can be combined with other explosive detection system(s) to improve their joint statistical probabilities (reduce false alarm rate, for example) by considering a joint algorithm which processes the TD-THz data map from the system 10 and the other system(s) data map. The other systems may be two-dimensional single or multi-view transmission X-ray at one or more energies, back-scatter X-Ray, computed tomography X-Ray, thermal-neutron scattering, thermograph, MRI, quadrupole resonance, millimeter wave imaging, and or other explosive detection systems.

Figure 7:
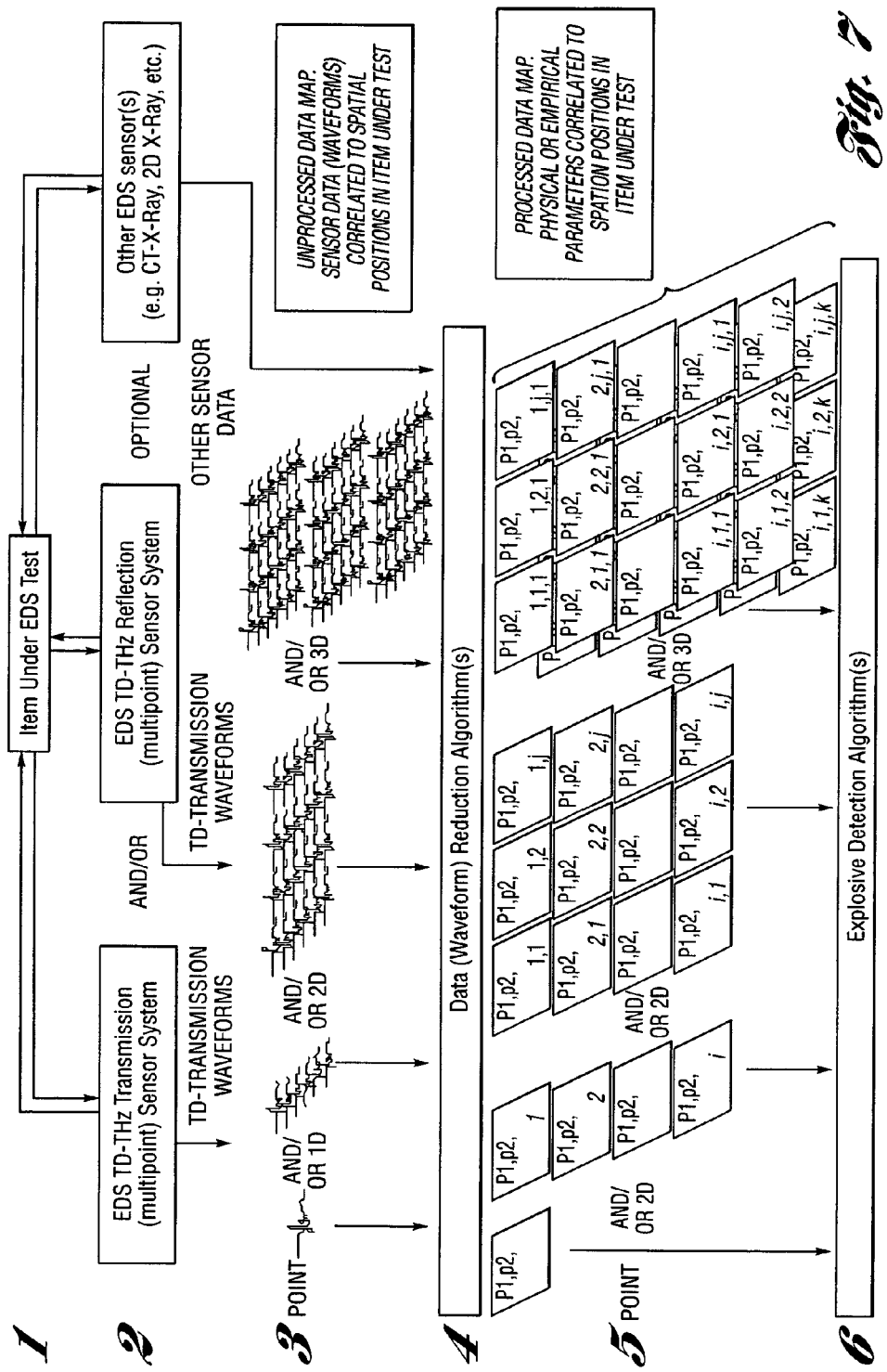
FIG. 7 depicts a multilevel interrogation process of the system in accordance with the invention.

The relationship of each of levels of detection of the system 10 is shown in FIG. 7. Specifically, Level 1 An item under test may or may not have an explosive configuration present.

Level 2 The system 10 uses one or more TD-THz transmitters and receivers in a transmission configuration, isolated or in a 1-, 2- or 3- dimensional array configured to acquire THz waveforms from one or more spatial locations on the item under test; and/or one or more TD-THz transmitters and receivers in a reflection configuration, isolated or in a 1-, 2- or 3-dimensional array configured to acquire THz waveforms from one or more spatial locations on the item under test; and, optionally, one or more other sensors (such as X-Ray and CT X-Ray) which acquire data capable of providing discrimination between explosives and benign material from a single point or a 1-, 2- or 3-dimensional spatial matrix within the sample. These sensors acquire data from Level 1 and provide data to level 3.

Level 3 Here, unprocessed data map consisting of point and/or 1-, 2-, and/or 3-dimensional matrices of transmission, and/or reflection THz waveforms are correlated spatially to the item under test from level 2, and/or equivalent data maps from other sensors (such as X-Ray, CT X-Ray sensors, mass spectrometry and metal detection).

Level 4 In this level, data reduction algorithms process the data map from level 3 into point or 1-, 2-, or 3-dimensional matrices of physical or empirical parameters correlated spatially to the item under test.

Level 5 Next, one or more points and 1-, 2-, and 3-dimensional matrices of one or more physical parameters per location are correlated spatially to locations within the item under test. This map $[(p1,p2,\ldots)$ and/or $(p1,p2,\ldots)_i$ and/or $(p1,p2,\ldots)_{ij}$ and/or $(p1,p2,\ldots)_{i,j,k}]$ is then utilized by explosive detection algorithm in level 6.

Level 6 An algorithm or combined set of algorithms utilize the data map from Level 5 and apply statistical multivariable criteria on one or more parameters with one or more rules for analyzing the entire map or part of the map to achieve an acceptable true positive probability and false positive probability.

In certain implementations, the processor 21 may be implemented with algorithms that analyze the time-of-flight properties of the terahertz radiation. The time-of-flight analysis may be combined with the three dimensional images to determine the bulk properties of the article under investigation. The time-of-flight may also be correlated with the reflection radiation to obtain unique signatures of a component or material in the article being investigate.

Other embodiments are within the scope of the following claims.

What is claimed is:

1. A system to detect an article comprising:
one for more terahertz modules, each module either generating or receiving, or both generating and receiving, terahertz radiation, some of the terahertz radiation being reflected from the article and the remainder of the terahertz radiation being transmitted through the article;

a processor configured to convert the transmitted and reflected terahertz radiation to a plurality of voxels, and assign each voxel of the plurality of voxels a location within a volume and a signature, wherein the signature indicates a material characteristic, and characterize the article based on the location of the plurality of voxels within the volume and the signatures of each voxel of the plurality of voxels; and wherein the processor is further configured to determine if the article is an explosive device based on the location of the plurality of voxels within the volume and the signatures of each voxel of the plurality of voxels.

2. The system of claim 1 wherein the transmitted terahertz radiation is analyzed for spectral signatures of the article.

3. The system of claim 1 wherein the transmitted terahertz radiation is analyzed for attenuation of the transmitted radiation.

4. The system of claim 1 wherein the transmitted terahertz radiation is analyzed for the time delay of the transmitted radiation.

5. The system or claim 1 wherein the reflected terahertz radiation is reflected from at least one interface between the article and another material.

6. The system of claim 1 wherein the reflected terahertz radiation is analyzed for spectral signatures of the article.

7. The system of claim 1 wherein the reflected terahertz radiation is analyzed for the time delay of the reflected radiation.

8. The system of claim 1 wherein the reflected terahertz radiation is analyzed for the attenuation of the reflected radiation.

9. The system of claim 1 further comprising a source which produces optical pulses, at least one of said terahertz modules processing the optical purses to generate terahertz radiation.

10. The system of claim 1 further comprising a source which produces continuous wave optical radiation, at least one of said terahertz modules processing the continuous wave optical radiation to generate terahertz radiation.

11. The system of claim 1 wherein multiple terahertz modules are configured as a first array of terahertz modules.

12. The system of claim 11 further comprising a second array of terahertz modules, each module of the second array of terahertz modules either generating or receiving, or both generating and receiving, terahertz radiation.

13. The system of claim 1 wherein the processor is implemented with an algorithm that performs the analysis on the terahertz radiation information.

14. The system of claim 1 further comprising one or more other diagnostics to augment the terahertz radiation information analyzed by the processor.

15. The system of claim 14 wherein the other diagnostics is selected from the group consisting of mass spectrometry, X-ray, and metal detection.

16. The system of claim 1 wherein the processor analyzes the time-of-flight of the terahertz radiation and correlates the time-of-flight of the reflection radiation to obtain signatures unique to a component of the article.

17. The system of claim 1 wherein the terahertz modules operate in the range between about 0.01-10 THz.

18. The system of claim 1, wherein the processor is further configured to characterize the article by determining if the number of voxels located within the volume is above a threshold value.

19. The system of claim 1, wherein the processor is further configured to characterize the article by determining if the plurality of voxels are sufficiently contiguous within the volume.

20. A method to detect an article comprising:

generating or receiving, or both generating and receiving, terahertz radiation from One or more terahertz modules, some of the terahertz radiation being reflected from the article and the remainder of the terahertz radiation being transmitted through the article;

converting the transmitted and reflected terahertz radiation to a plurality of voxels, assigning each voxel of the plurality of voxels a location within a volume and a signature, wherein the signature indicates a material characteristic;

characterizing the article based on the location of the plurality of voxels within the volume and the signatures of each voxel of the plurality of voxels; and characterizing the article by determining if the article is an explosive device based on the location of the plurality of voxels within the volume and the signatures of each voxel of the plurality of voxels.

21. The method of claim 20 further comprising producing optical pulses, at least one of said terahertz modules processing the optical pulses to generate terahertz radiation.

22. The method of claim 20 further comprising producing continuous wave optical radiation, at least one of said terahertz modules processing the continuous wave optical radiation to generate terahertz radiation.

23. The method of claim 20 further comprising analyzing the time-of-flight of the terahertz radiation and correlating the time-of-flight of the reflection radiation to obtain signatures unique to a component of the article.

24. The method of claim 20 wherein the terahertz modules operate in the range between about 0.01-10 THz.

25. The method of claim 20, further comprising the step of characterizing the article by determining if the number of voxels located within the volume is above a threshold value.

26. The system of claim 20, wherein the processor is further configured to characterize the article by determining if the plurality of voxels are sufficiently contiguous within the volume.

* * * * *

UNITED STATES PATENT AND TRADEMARK OFFICE
CERTIFICATE OF CORRECTION

PATENT NO. : 7,449,695 B2 Page 1 of 1
APPLICATION NO. : 11/138246
DATED : November 11, 2008
INVENTOR(S) : David A. Zimdars et al.

It is certified that error appears in the above-identified patent and that said Letters Patent is hereby corrected as shown below:

In column 12, claim 1, line 66, before "more terahertz" delete "for" and substitute --or-- in its place.

In column 13, claim 9, line 37, after "processing the optical" delete "purses" and substitute --pulses-- in its place.

In column 14, claim 20, line 17, after "radiation from" delete "One" and substitute --one-- in its place.

Signed and Sealed this

Twenty-first Day of April, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,449,695 B2 | Page 1 of 1 |
| APPLICATION NO. | : 11/138246 | |
| DATED | : November 11, 2008 | |
| INVENTOR(S) | : David A. Zimdars et al. | |

It is certified that error appears in the above-identified patent and that said Letters Patent is hereby corrected as shown below:

On the Title Page

Item (73), delete "Picometrix," and substitute --Picometrix, LLC,-- in its place.

Signed and Sealed this

Twenty-seventh Day of October, 2009

David J. Kappos
*Director of the United States Patent and Trademark Office*